US007364880B2

(12) United States Patent
Ray et al.

(10) Patent No.: US 7,364,880 B2
(45) Date of Patent: Apr. 29, 2008

(54) INTEGRATION OF AT LEAST TWO PROCESSES TO RE-USE ACID

(75) Inventors: Charles David Ray, Ottumwa, IA (US); John A. Bohlmann, Ottumwa, IA (US); Don Grunig, Oskaloosa, IA (US); James R. Trinkle, Bussey, IA (US); Michael Brandon Bassett, Sparks, NV (US)

(73) Assignee: Cargill, Incorporated, Wayzata, MN (US)

( * ) Notice: Subject to any disclaimer, the term of this patent is extended or adjusted under 35 U.S.C. 154(b) by 288 days.

(21) Appl. No.: 10/503,018

(22) PCT Filed: Jan. 31, 2003

(86) PCT No.: PCT/US03/02970

§ 371 (c)(1),
(2), (4) Date: Jul. 28, 2004

(87) PCT Pub. No.: WO03/066186

PCT Pub. Date: Aug. 14, 2003

(65) Prior Publication Data

US 2005/0148052 A1     Jul. 7, 2005

Related U.S. Application Data

(60) Provisional application No. 60/353,718, filed on Feb. 1, 2002.

(51) Int. Cl.
*C12P 19/28* (2006.01)
*C12P 7/48* (2006.01)
*C12M 1/00* (2006.01)

(52) U.S. Cl. .................. 435/84; 435/144; 435/289.1

(58) Field of Classification Search .............. 435/84, 435/144, 289.1
See application file for complete search history.

(56) References Cited

U.S. PATENT DOCUMENTS

| 5,268,283 | A | * | 12/1993 | Mothes et al. | ............. | 435/144 |
| 5,969,175 | A | * | 10/1999 | Murao et al. | ............. | 558/411 |
| 6,137,004 | A | * | 10/2000 | McQuigg et al. | ........... | 562/580 |
| 6,514,414 | B1 | * | 2/2003 | Martin | ........... | 210/670 |
| 2002/0115639 | A1 | * | 8/2002 | Fan et al. | ................. | 514/62 |
| 2004/0091973 | A1 | * | 5/2004 | Deng et al. | ................. | 435/84 |

\* cited by examiner

*Primary Examiner*—Herbert J. Lilling
(74) *Attorney, Agent, or Firm*—Klarquist Sparkman, LLP

(57) ABSTRACT

The invention relates to integrating at least two processes that use at least one acid, wherein one process utilizes an ion-exchange purification step.

10 Claims, 1 Drawing Sheet

INTEGRATION OF AT LEAST TWO PROCESSES TO RE-USE ACID

CROSS REFERENCE TO RELATED APPLICATIONS

This is the U.S. National Stage of International Application No. PCT/US03/02970, filed Jan. 31, 2003, which was published in English under PCT Article 21(2), which in turn claims the benefit of U.S. Provisional Application No. 60/353,718, filed Feb. 1, 2002. Both applications are incorporated herein in their entirety.

FIELD

The invention relates to integrating at least two processes that use acid, wherein one process utilizes an ion-exchange purification step.

BACKGROUND

The disposal of liquid waste that contains high concentrations of caustic and/or corrosive materials (ion-containing material) may cause serious environmental problems. Therefore, producers of such waste may take steps to either remove the caustic or corrosive material, or treat the material to convert it to less harmful compounds. Cost associated with the disposal of such waste reduces the profit that can be achieved from products that use caustic or corrosive materials in their production.

Ion-containing materials are frequently used in processes employing ion-exchange purification. Products, such as, citric acid, itaconic acid, water, sugars and/or, sugar alcohols are purified using ion-exchange. Ion-containing materials are used to contact the ion-exchange resin and "recharge" the resin so that it can be repeatedly used to remove contaminants from the product.

SUMMARY

The invention provides methods that use the same acid in multiple production processes (processes that give rise to distinct products), which reduces the overall cost of the acid (eliminates the need to purchase more than once), and reduces the overall disposal cost associated with the acid (need to dispose of less). Additional savings can be achieved when additional ingredients can be shared between the multiple production processes. For example, production processes that produce biomass and require ion-exchange purification can be coupled to processes that use biomass and one or more acids.

For example, acids, such as HCl, $H_2SO_4$, or any strong acid, can be used to prepare glucosamine from chitin containing biomass, as well as from bacteria. The processes that produce glucosamine can be integrated with processes that utilizes ion-exchange technology, so that the acid can be used to generate a first product (for example, glucosamine) and then the acid can be used to regenerate an ion-exchange resin which is used to purify a product such as citric acid, bacterial produced proteins, etc. Hence, the acid is used at least twice to make two products, one product that requires treatment with acid and one product that requires ion-exchange purification.

Accordingly, one aspect of the invention provides a process involving contacting an acid with biomass, wherein at least one first product is formed, then collecting such as by distillation, membrane separation, and/or chromatography, the acid and contacting the acid with an ion-exchange resin to regenerate the resin, wherein the ion-exchange resin is used to purify a second product.

Another aspect of the invention provides using the biomass that produced the second product as a component of the first process (see FIG. 1). Hence, both the biomass and the acid are used in both the first and second process.

Specific examples of processes that can be coupled include organic acid production and glucosamine production. Additional benefits can be obtained by using caustic materials, such as, NaOH, $NH_4OH$ and/or KOH, that may be used to remove proteins from the biomass, to adjust the pH of acids used in the integrated processes.

DETAILED DESCRIPTION

Figure 1:
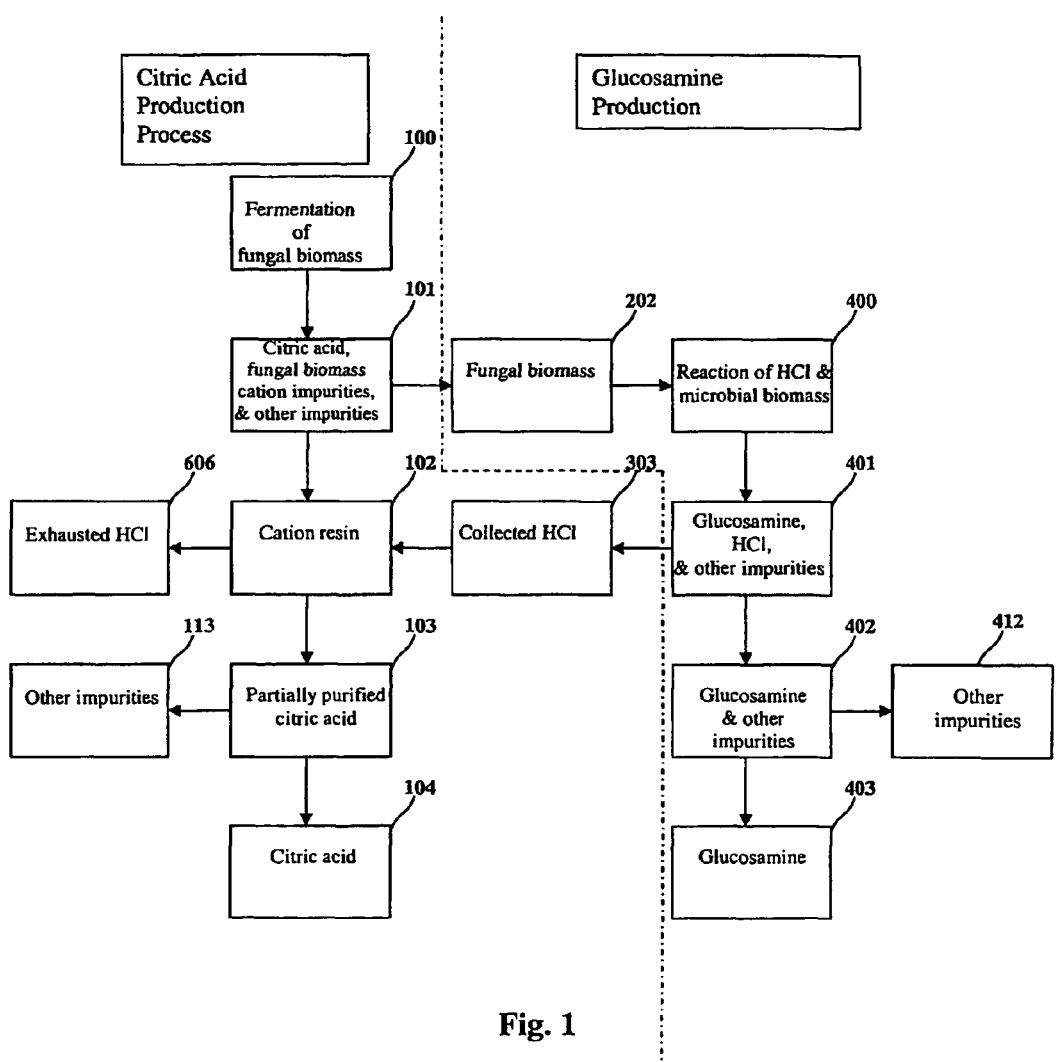
FIG. 1 is a diagram that displays a general schematic illustration of a citric acid producing process coupled to a glucosamine producing process. The dotted line illustrates where these processes would be separated if they were not integrated.

As described above, the disclosed processes integrate what were previously two separate processes together by using one or more of the same components in both processes. One of the shared components is an acid. Additional shared components can be biomass, water, and/or caustic solutions.

Acids

The acid can be any acid that is capable of forming a product, then being collected, and then used to regenerate an ion-exchange resin. Ion-exchange resins that may be regenerated include for example, Amberlite IR 120 (available from Rohm and Haas Co.), Duolite C-291 (available from The Dow Chemical Co.), Amberlite 200 (available from Rohm and Haas Co.), and Lewatit SP-112 (available from Bayer Ag.). As used herein "spent ion-exchange resin" refers to when the resin becomes loaded with charged contaminants to the point where unacceptable amounts of charged contaminants pass through the resin. One of ordinary skill in the art will appreciate that the acceptability of contaminant concentrations varies with the product being purified. Thus when the resin fails to remove the desired amount of charged contaminants it is termed "spent" and subjected to regeneration (described below).

Typically, the binding capability of a particular resin is monitored by comparing the ion content of the effluent to the ion content of the feed. When the ion content of the effluent equals that of the feed the resin is said to be exhausted.

The acid can be used first as a component in a first process and then used to regenerate the ion-exchange resin for a second process, or the acid can be used first to regenerate the ion-exchange resin, and then as a component in a second process. The acid can also be cycled through the first and second processes multiple times.

When using HCl in a combined glucosamine/citric acid production process acid concentrations above about 1, 2, 3, 4, 5, 7, 10, 15, and 35% are desired to feed into the biomass process, and acid concentrations for regenerating the resin can range from about 4-10%.

The acid is then recollected and its concentration may be adjusted (diluted for example by adding water, or concentrated for example by adding concentrated acid or removing water) to make it useful for regenerating the ion-exchange resin. Accordingly, if the acid is used to regenerate the resin first its concentration may need to be adjusted for use in the biomass treatment.

The integration of the two processes can actually occur between two portions of a plant that are operated independently of each other (by separate parties). Furthermore, the acid can be additionally used in subsequent processes, for example the acid can also be used to regenerate ion resins that are used to purify water.

Biomass

Biomass as used herein refers to cells and byproducts made by cells (such as, intercellular organelles, nucleic acid, protein, cells walls, shells, and exoskeletons). Biomass can be derived from, for example, bacteria, yeast, fungus, plants, and shellfish. Biomass can be living, or dead. During many production processes live biomass is used to generate products, such as beer, citric acid, and/or pharmaceuticals. Generally, the living biomass eventually reaches a peak production level and then production of the desired product diminishes. The living biomass then becomes a waste product that needs to be disposed of. The remaining biomass material (cell bodies from fermentation or shells from shellfish) is then generally considered a waste product and sold as an animal feed or fertilizer.

Both fungal biomass and bacterial biomass when treated with acid will yield glucosarnine, a beneficial dietary supplement and/or food ingredient. The fungal and bacterial biomass can be generated from citric acid production or lactic acid production, respectively.

Integrated Plant

A diagram that displays a general schematic illustration of an integrated plant for producing glucosamine and citric acid according is shown in FIG. 1.

Fermentation of the fungal biomass occurs at 100. The production of citric acid is generally depicted by a flow from 100 to 101 to 102 to 103 to 104. Fungal biomass is removed at 101. Cations are removed at 102 to partially purify the citric acid. Other impurities are removed at 103, and the resultant citric acid is collected at 104.

The production of glucosamine is generally depicted by a flow from 400 to 401 to 402 to 403. Hydrochloric acid is removed at 401. Other impurities are removed at 402, and the resultant glucosamine is collected at 403.

The fungal biomass removed at 101 is supplied via 202 as the microbial biomass for the production of glucosamine at 400.

The hydrochloric acid removed at 401 is supplied via 303 to regenerate the cation resin at 102. After regenerating the cation resin, exhausted hydrochloric acid is removed at 606.

Specific details concerning pipes, valves, reaction vessels, and other engineering articles used to implement the embodiment of FIG. 1 are not critical. For example, a valving arrangement can be used to control the flow of citric acid production at 102. As a particular illustration, valves could be closed when the cation resin is spent to isolate the cation resin at 102 from section 101 and section 103. Other valves could then be opened to allow flow of hydrochloric acid from 303 through 102 to 606 to regenerate the cation resin. It should be understood that other numbered areas, such as pipes, valves, reaction vessels, and other engineering articles, could be explicitly added to the diagram of FIG. 1 to provide for flushes, rinses, purifications, and other routine engineering processes used to implement the embodiment of FIG. 1. However, after understanding the diagram of FIG. 1 and the disclosure provided herein, one skilled in the art will easily envision such pipes, valves, reaction vessels, and other engineering articles to implement the invention.

EXAMPLE

This example illustrates a general process for using biomass from citric acid production to make glucosamine, collecting the acid from glucosamine production, using the acid to regenerate an ion-exchange resin and then using the resin to purify citric acid.

Biomass, from a citric acid fermentation process, was mixed with concentrated hydrochloric acid to form a mixture of 10 to 15 percent hydrochloric acid and 5 to 6 percent biomass, based upon dry weight of the biomass. The mixture was heated at reflux. Samples were taken from time to time, and the reaction analyzed with a high-pressure liquid chromatograph available from Dionex HPLC under the trade designation "DX-500." Results indicated that glucosamine was produced.

Following the reaction, the mixture was filtered. The filtrate comprised glucosamine and hydrochloric acid. The filtrate was evaporated using a rotating evaporator manufactured by RotaVap to increase the glucosamine concentration of the solution. The aqueous hydrochloric acid evaporate was then collected for reuse.

After the citric acid solution flow has been redirected (is no longer flowing through the resin), the spent resin is regenerated using the recovered aqueous HCl. Regeneration is accomplished by feeding about 7% aqueous hydrochloric acid solution counter-current, or co-current, to the normal process flow into the resin to regenerate the resin. The hydrochloric acid is supplied as a uniform flow by a pump that controls the driving pressure for the regeneration flow. Typical amounts of regeneration flow range from 2 to 12 pounds of HCl per cubic foot of resin. Typical temperatures for the regeneration flow range from 100° F. to 135° F. Typical mass flow rates for the regeneration flow range from 2 to 10 resin bed volumes per hour. After flowing through the resin, the hydrochloric acid can be neutralized appropriately and sent to an appropriate sewer.

After the above regeneration step, the 7% aqueous hydrochloric acid flow is stopped and acid remaining in the resin is displaced from the resin bed by water. This water flow is followed by a series of flushes or rinses to remove remaining acid.

The cation resin of the column is now regenerated. It is ready to receive a new flow of citric acid containing solution, which again comprises citric acid, cation impurities, and other citric acid impurities.

The processes described in the above example are representative of particular processes of the invention. The illustrated processes are intended to help explain the invention, but should not be considered limitations of the invention.

What is claimed is:

1. A method for combining methods to re-use an acid, the method comprising:
   (a) forming glucosamine by contacting a chitin-containing biomass with a first acid;
   (b) collecting acid remaining after the first acid contacts the chitin-containing biomass;
   (c) separating the collected acid of (b) from glucosamine present therein;
   (d) providing a spent ion-exchange resin; and
   (e) regenerating the spent ion-exchange resin using the acid separated from the glucosamine.

2. The method according to claim 1, wherein the acid comprises hydrochloric acid, sulfuric acid, phosphoric acid or a mixture thereof.

3. The method according to claim 1, further comprising producing a second acid comprising citric acid by fermenting the chitin-containing biomass of (a) before contacting the chitin-containing biomass with the first acid.

4. The method according to claim 1, wherein the chitin-containing biomass is a fungal biomass.

5. The method according to claim 1 further comprising (f) collecting the acid used to regenerate the spent ion-exchange resin.

6. The method according to claim 5, wherein the collected acid from step (f) is used to form glucosamine by contacting a fungal biomass with the collected acid.

7. The method according to claim 3, further comprising using the regenerated ion-exchange resin to purify the citric acid produced by the fermenting of the chitin-containing biomass.

8. The method according to claim 7 further comprising displacing citric acid remaining in the regenerated ion-exchange resin by use of water.

9. The method according to claim 1, further comprising refluxing the chitin-containing biomass and first acid to form the glucosamine.

10. A method for re-use of acid comprising:
    (a) fermenting a fungal biomass to produce citric acid;
    (b) separating the citric acid from the fungal biomass;
    (c) purifying the citric acid separated from the fungal biomass using an ion-exchange resin;
    (d) forming glucosamine by contacting the fungal biomass separated from the citric acid in (b) with an acid comprising hydrochloric acid, sulfuric acid, phosphoric acid or a mixture thereof;
    (e) collecting the acid that contacted the fungal biomass in (d);
    (f) separating glucosamine in the collected acid of (e); and
    (g) regenerating the ion-exchange resin after purifying the citric acid by using the acid separated from the glucosamine.

* * * * *

UNITED STATES PATENT AND TRADEMARK OFFICE
CERTIFICATE OF CORRECTION

PATENT NO. : 7,364,880 B2  Page 1 of 1
APPLICATION NO. : 10/503018
DATED : April 29, 2008
INVENTOR(S) : Charles David Ray et al.

It is certified that error appears in the above-identified patent and that said Letters Patent is hereby corrected as shown below:

On the Title Page Item (56) In the References Cited:

In the citation for the Deng et al. reference, "2004/0091973 A1*" should read --2004/0091976 A1*--.

Column 3, line 27, "glucosarnine," should read --glucosamine,--.

In the Claims:

Column 6, line 17, "acid of(e);" should read --acid of (e)--.

Signed and Sealed this

Thirtieth Day of November, 2010

David J. Kappos
*Director of the United States Patent and Trademark Office*